United States Patent [19]

Smith et al.

[11] Patent Number: 4,748,275

[45] Date of Patent: May 31, 1988

[54] NON-HYGROSCOPIC TRIALKYLAMINE OXIDES

[75] Inventors: Kim R. Smith; James E. Borland, both of Baton Rouge, La.

[73] Assignee: Ethyl Corporation, Richmond, Va.

[21] Appl. No.: 904,289

[22] Filed: Sep. 8, 1986

[51] Int. Cl.$^4$ .......................................... C07C 135/02
[52] U.S. Cl. ................................... 564/298; 564/297; 564/463
[58] Field of Search ....................... 564/297, 298, 299

[56] References Cited

U.S. PATENT DOCUMENTS

| | | | |
|---|---|---|---|
| 3,047,579 | 7/1962 | Witman | 564/297 X |
| 3,270,060 | 8/1966 | Wakeman et al. | 564/297 |
| 3,283,007 | 11/1966 | Chadwick | 564/298 |
| 3,330,327 | 7/1967 | Kennedy et al. | 564/298 X |
| 3,333,000 | 7/1967 | Albert et al. | 564/298 |
| 3,471,562 | 10/1969 | Wakeman et al. | 564/298 X |
| 3,558,710 | 1/1971 | Stalioraitis et al. | 564/298 |

FOREIGN PATENT DOCUMENTS

| | | | |
|---|---|---|---|
| 704364 | 2/1965 | Canada | 564/298 |
| 1518104 | 5/1974 | Fed. Rep. of Germany | 564/258 |
| 1066763 | 4/1967 | United Kingdom | 564/298 |

*Primary Examiner*—Robert V. Hines
*Attorney, Agent, or Firm*—John F. Sieberth; J. D. Odenweller

[57] ABSTRACT

A solid non-hygroscopic flakeable di-$C_{14-30}$ alkyl $C_{1-2}$ alkylamine oxide is made by reacting di-$C_{14-30}$ alkyl $C_{1-2}$ alkylamine with aqueous hydrogen peroxide containing at least 40 weight percent $H_2O_2$ in the absence of a solvent.

8 Claims, No Drawings

NON-HYGROSCOPIC TRIALKYLAMINE OXIDES

BACKGROUND OF THE INVENTION

Trialkylamine oxides are made by reacting trialkylamines with hydrogen peroxide. They are useful for many purposes such as in hair conditioners and shampoos as described in U.S. Pat. No. 3,086,943. When a $C_{10-16}$ alkyl dimethylamine oxide as described in U.S. Pat. No. 3,086,943 is made, the products will gel if the concentration of the amine oxide exceeds about 30 weight percent. Alkyl dimethylamine oxides are described in Kirk-Othmer "Encyclopedia of Chemical Technology", 3rd Ed. At page 266, Kirk-Othmer states that "when a strictly aqueous system is employed, final concentrations of amine oxide should be limited to below 35% since higher concentrations tend to gel and prevent good mixing."

Hoh et al., J. Am. Oil Chem. Soc., 40 (1963) page 268–271 describe the synthesis of dimethyl dodecylamine oxide by reaction of dimethyl dodecylamine with 35% aqueous hydrogen peroxide. The product is a 30–40 weight percent aqueous solution of the amine oxide. Hoh et al. note that even using 35% aqueous hydrogen peroxide, the reaction mixture will gel unless diluted with water during the reaction.

Hoh et al. attempted to make dimethyl dodecylamine oxide without co-feeding water starting with 35%, 70% and 90% aqueous hydrogen peroxide. With 35% and 70% hydrogen peroxide, the product was a gel that could not be stirred. The reaction with 90% hydrogen peroxide was not completed because of darkening of the reaction mixture.

Chadwick U.S. Pat. No. 3,215,741 describes the preparation of di-$C_{1-2}$ alkyl $C_{10-20}$ alkylamine oxides by reaction of the tert-amine with hydrogen peroxide. While attempting to make the desirable concentrated solutions of the amine oxide, Chadwick found that when commercially available hydrogen peroxide containing 20–90 weight percent $H_2O_2$ was used, the reaction sets up to a gel resembling a thick starch paste long before completion of the reaction. Chadwick's solution to the problem was to co-feed at least 20% hydrogen peroxide and sufficient water to the tert-amine such that the final product was water diluted. When dimethyl dodecylamine was used the most concentrated amine oxide solution that could be obtained was only 30–40 weight percent amine oxide.

A need exists for a solid non-hygroscopic flakeable trialkylamine oxide. Such materials would be useful as fabric softeners in laundry detergents. Statioraitis et al. U.S. Pat. No. 3,776,959 describes a process for making a solution of various amine oxides in a non-polar solvent such as toluene by dissolving a tert-amine in the non-polar solvent and adding aqueous hydrogen peroxide while removing water by azeotropic distillation. The product is a solution in an organic solvent. Such solutions could not be used in dry solid laundry detergent formulations.

SUMMARY OF THE INVENTION

In co-pending application Ser. No. 821,793, filed Jan. 23, 1986 there is described a process for making a concentrated aqueous gel-free solution of a di-$C_{6-12}$ alkyl methylamine oxide by reacting di-$C_{6-12}$ alkyl methylamine with aqueous hydrogen peroxide containing at least 40 weight percent $H_2O_2$. In this manner a gel-free aqueous solution containing 80 weight percent or more di-$C_{6-12}$ alkyl methylamine oxide can be prepared.

It has now been discovered that solid non-hygroscopic flakeable trialkylamine oxides can be made from di-$C_{14-24}$ alkyl $C_{1-2}$ alkylamine by reaction with aqueous hydrogen peroxide containing at least 40 weight percent $H_2O_2$ in the absence of a solvent and at a temperature high enough to maintain the product in a molten state. The molten product can be processed in a conventional drum flaker to produce a flaked product suitable for use in laundry detergent formulations.

DESCRIPTION OF THE PREFERRED EMBODIMENTS

A preferred embodiment of the invention is a process for making a solid non-hygroscopic flakeable di-$C_{14-24}$ alkyl $C_{1-2}$ alkylamine oxide, said process comprising reacting a di-$C_{14-24}$ alkyl $C_{1-2}$ alkylamine with at least a stoichiometric amount of aqueous hydrogen peroxide containing initially at least 40 weight percent $H_2O_2$ in the absence of a solvent.

The tert-amine oxides that can be made as non-hygroscopic flakeable solids are those having the formula

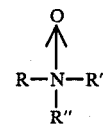

wherein R and R' are alkyl groups containing from 14 to about 30 carbon atoms, more preferably 14 to about 24 carbon atoms and R" is a methyl or ethyl group. The alkyl groups are preferably linear but may have some branching not to exceed about two side branches. Some examples of the amine oxides are:
ditetradecyl methylamine oxide
di-(2-ethyloctadecyl) methylamine oxide
tetradecyl octadecyl ethylamine oxide
ditriacontyl methylamine oxide and the like.

The lower alkyl group can be either methyl or ethyl but is preferably methyl. Some further examples of the tertiary amines are:
ditetradecyl methylamine
tetradecyl eicosyl ethylamine
dioctadecyl methylamine
dieicosyl methylamine
ditetracosyl methylamine
ditetradecyl ethylamine
dihexadecyl ethylamine
hexadecyl octadecyl methylamine
dioctadecyl ethylamine
docosyl tetracosyl methylamine
didocosyl methylamine and the like including mixtures thereof.

In a more preferred embodiment, the R and R' groups contain 14 to 18 carbon atoms and R" is methyl. These include:
ditetradecyl methylamine
dihexadecyl methylamine
dioctadecyl methylamine
tetradecyl hexadecyl methylamine
hexadecyl octadecyl methylamine
tetradecyl octadecyl methylamine and the like.

In a still mor preferred embodiment R and R' are normal alkyl groups. Most preferably R and R' are normal alkyl groups containing 14–18 carbon atoms or mixture thereof. The preferred hydrogen peroxide solutions are at least 40 weight percent $H_2O_2$ and more preferably at least 50 weight percent $H_2O_2$. More concentrated hydrogen peroxide solutions can be used up to about 70 weight percent $H_2O_2$ or even 90 percent $H_2O_2$ if adequate safety precautions are observed. The most preferred hydrogen peroxide concentration is about 50 weight percent $H_2O_2$.

The amount of aqueous hydrogen peroxide should be at least about a stoichiometric amount. For example at least about 0.9 moles and preferably 1.0 moles of hydrogen peroxide per mole of tert-amine. Good results can be achieved using about 1.1–1.3 mole parts of aqueous hydrogen peroxide per mole of tert-amine and more preferably about 1.15–1.25 mole parts of hydrogen peroxide per mole of tert-amine.

The reaction is conducted by adding the concentrated aqueous hydrogen peroxide to the stirred tert-amine. Inclusion of a small amount of a chelating agent such as diethylene triaminepentaacetic acid improves the reaction rate. The reaction temperature can vary from ambient up to 100° C. or higher. The reaction can be started at a moderate temperature, e.g. 25°–60° C., and the temperature slowly increased as the reaction proceeds. Towards the end of the reaction the temperature is increased to 90° C. or higher as required to maintain a molten reaction mass. Above atmospheric pressure may be required with the higher alkyl amines to achieve a temperature sufficient to melt the product.

Addition time will depend on temperature and scale. Preferably the hydrogen peroxide addition is not so rapid that a large accumulation of unreacted hydrogen peroxide occurs. Addition times in the range of 0.1–8 hours for small scale runs (on the order of 1 liter) up to 1–24 hours for large scale commercial operations are generally satisfactory.

Following the hydrogen peroxide addition, the reaction mixture can be stirred at 60° C. or higher for a period to be certain that the reaction has gone to completion. A ride time of about 1–24 hours is usually adequate. Following this, any unreacted hydrogen peroxide can be decomposed by adding a stoichiometric amount of a reducing agent such as $Na_2SO_3$.

The following example shows how the process can be carried out.

EXAMPLE

In a reaction vessel was placed 44.7 grams of dioctadecyl methylamine (amine value 94.9 mgKOH/g) and 0.05 grams of diethylenetriaminepentaacetic acid. This was heated with stirring to 65° C. and then 6.2 grams of 50 weight percent aqueous hydrogen peroxide was added dropwise over a 30 minute period. The mixture was then heated to 90° C. and stirred at that temperature for 4 hours. The mixture was then cooled forming a non-hygroscopic white solid melting at about 90° C. No tert-amine was detectable in the product indicating a 100% yield of dioctadecyl methylamine oxide.

We claim:

1. A process for making a solid non-hygroscopic flakeable di-$C_{14-24}$ alkyl $C_{1-2}$ alkylamine oxide, said process comprising reacting a di-$C_{14-24}$ alkyl $c_{1-2}$ alkylamine with at least a stoichiometric amount of aqueous hydrogen peroxide containing initially at least 40 weight percent $H_2O_2$ in the absence of a solvent or added water which when combined with aid aqueous hydrogen peroxide would lower the hydrogen peroxide concentration below 40 weight percent to form a reaction product which on cooling is said solid non-hygroscopic flakeable di-$C_{14-24}$ alkyl $C_{1-2}$ alkylamineoxide.

2. A process of claim 1 wherein said aqueous hydrogen peroxide contains at least 50 weight percent $H_2O_2$.

3. A process of claim 1 wherein said di-$C_{14-24}$ alkyl $C_{1-2}$ alkylamine is a di-$C_{14-24}$ alkyl methylamine and the product so produced is a di-$C_{14-24}$ alkyl methylamine oxide.

4. A process of claim 3 wherein said aqueous hydrogen peroxide contains at least 50 weight percent $H_2O_2$.

5. A process of claim 4 wherein said di-$C_{14-24}$ alkyl methylamine is dioctadecyl methylamine.

6. A process of claim 5 conducted at a temperature high enough to maintain the reaction mixture in a molten state.

7. A process of claim 1 conducted at a temperature high enough to maintain the reaction mixture in a molten state.

8. A process of claim 7 wherein said aqueous hydrogen peroxide contains about 50–70 weight percent $H_2O_2$.

* * * * *

UNITED STATES PATENT AND TRADEMARK OFFICE
CERTIFICATE OF CORRECTION

PATENT NO. : 4,748,275
DATED : MAY 31, 1988
INVENTOR(S) : KIM R. SMITH AND JAMES E. BORLAND

It is certified that error appears in the above-identified patent and that said Letters Patent is hereby corrected as shown below:

References Cited reads "1518104 5/1974" and should read -- 1518104 5/1970 --.

Column 2, line 41 reads "methylamihe" and should read -- methylamine --.

Column 2, line 66 reads "mor" and should read -- more --.

Column 4, line 17 reads "$c_{1-2}$" and should read -- $C_{1-2}$ --.

Column 4, line 21 reads "aid" and should read -- said --.

Signed and Sealed this

Sixteenth Day of August, 1988

Attest:

DONALD J. QUIGG

Attesting Officer      Commissioner of Patents and Trademarks